(12) United States Patent
Kim et al.

(10) Patent No.: US 11,364,092 B2
(45) Date of Patent: Jun. 21, 2022

(54) FIXING PIECE FIRING DEVICE FOR DENTAL MEMBRANE

(71) Applicant: MCTBIO Co., Ltd., Yongin-si (KR)

(72) Inventors: Sung Youn Kim, Seoul (KR); Jong Chan Lee, Namyangju-si (KR)

(73) Assignee: MCTBIO CO., LTD., Yongin-si (KR)

( * ) Notice: Subject to any disclaimer, the term of this patent is extended or adjusted under 35 U.S.C. 154(b) by 0 days.

(21) Appl. No.: 16/476,904

(22) PCT Filed: Mar. 8, 2019

(86) PCT No.: PCT/KR2019/002707
§ 371 (c)(1),
(2) Date: Jul. 10, 2019

(87) PCT Pub. No.: WO2020/091154
PCT Pub. Date: May 7, 2020

(65) Prior Publication Data
US 2021/0330423 A1 Oct. 28, 2021

(30) Foreign Application Priority Data

Oct. 30, 2018 (KR) .................. 10-2018-0131126

(51) Int. Cl.
*A61B 17/10* (2006.01)
*A61C 3/08* (2006.01)
*A61B 17/92* (2006.01)

(52) U.S. Cl.
CPC .............. *A61C 3/08* (2013.01); *A61B 17/10* (2013.01); *A61B 2017/925* (2013.01)

(58) Field of Classification Search
CPC ...... A61C 3/08; A61B 17/10; A61B 2017/925
USPC ............................................. 227/175.1, 147
See application file for complete search history.

(56) References Cited

U.S. PATENT DOCUMENTS

| 5,630,540 A * | 5/1997 | Blewett ............ A61B 17/07207 227/176.1 |
| 5,741,268 A * | 4/1998 | Schutz .................... A61B 17/68 606/104 |
| 6,273,893 B1 * | 8/2001 | McAllen, III ..... A61B 17/8872 606/104 |
| 6,402,759 B1 * | 6/2002 | Strong .................... A61B 17/92 81/463 |
| 6,840,943 B2 * | 1/2005 | Kennefick .............. A61B 17/92 606/104 |
| 2005/0070918 A1 * | 3/2005 | Zwirnmann .......... B25B 23/101 606/916 |

* cited by examiner

*Primary Examiner* — Michelle Lopez
(74) *Attorney, Agent, or Firm* — Lex IP Meister, PLLC

(57) ABSTRACT

The present invention relates to a fixing piece firing device for a dental membrane, the device being capable of firing the fixing piece to fix the dental membrane that covers a graft site after bone graft during implant surgery, and of facilitating access into an oral cavity due to a tip part with a curved front end, thus enabling a quick and easy procedure without using a typical dental drill.

3 Claims, 3 Drawing Sheets

FIXING PIECE FIRING DEVICE FOR DENTAL MEMBRANE

TECHNICAL FIELD

The present invention relates to a fixing piece firing device for a dental membrane, the device being capable of firing the fixing piece to fix the dental membrane that covers a graft site after bone graft during implant surgery, and of facilitating access into an oral cavity due to a tip part with a curved front end, thus enabling a quick and easy procedure without using a typical dental drill.

BACKGROUND ART

When a tooth is extracted, the extracted tooth is replaced with a false tooth, or a dental bridge surgery is performed in which surrounding teeth are used as anchors and a dental bridge involving crowns is attached to the surrounding teeth to fill a gap where the tooth is extracted. However, such a dental prosthesis such as a false tooth or a dental bridge that results from such a procedure has various problems, including a low masticatory force compared with an original tooth, an adverse influence on surrounding teeth, and the like.

Due to this, recently, a dental implant surgery in which a prosthesis is implanted in an alveolar bone has been widely performed. Such a dental implant surgery is a procedure that implants a tooth root prosthesis in the alveolar bone to bond a prosthesis that is customized to look and function like a real tooth and the bone together, thus enabling a patient to obtain the same effect as using a real tooth.

In the implant surgery, an implant hole is formed in the alveolar bone where a tooth is missing, and then a fixture is implanted into the hole. At this time, a tapping operation is selectively performed to firmly implant the fixture in the hole. Then, after implanting the fixture into the hole, a cover screw is coupled to the fixture to prevent foreign substances from penetrating into the fixture, and the gum tissue is sutured, thus finishing a first-stage surgery. Then, after about three or six months elapse, an incision is made in the gum tissue and the cover screw is removed from the fixture. Then, a healing abutment is selected by taking into consideration to the type of abutment to be coupled to the fixture and then is coupled to the fixture, thus finishing a second-stage surgery. The healing abutment serves to help the gum tissue heal cleanly around the fixture before the abutment is coupled to the fixture. When the gum tissue is fully healed after about two or three weeks from the time at which the healing abutment is coupled, the healing abutment is removed from the fixture and a final abutment is coupled to the fixture. Then, a mold is made to make a prosthesis, and a final prosthesis that matches a shape of a natural tooth to be replaced is coupled onto the abutment, thus completing the implant surgery.

However, in a general implant surgery, when the alveolar bone is partially defective and it is difficult for the remaining alveolar bone to sufficiently support the fixture, a bone graft material is used to fill in a bone defect site. Then, an additional procedure is performed to enable the bone graft material to function as a new alveolar bone. That is, a procedure that guides alveolar bone growth at sites with insufficient bone is performed. This procedure is called guided bone regeneration (GBR).

In order to perform GBR, a fixture is first inserted into the alveolar bone, a bone defect site is filled with a bone graft material, and then a dental membrane is placed thereover to enable the bone graft material to maintain a desired shape. Then, the dental membrane is fixed to a desired location by using a predetermined fixing means, usually using a fixing piece. For this purpose, the dental membrane has multiple through holes formed therein. The fixing piece is placed between the through holes, and then the fixing piece is firmly secured into the alveolar bone or bone graft material by using a dental drill.

However, there are often cases where the dental drill fails to access an implant site depending on the position of the site, causing a problem that it is difficult for the dentist to accurately fix the fixing piece to the site. Additionally, the fixing piece for membrane fixation has a disadvantage in that it is difficult to use with the dental drill because of small size thereof.

DISCLOSURE

Technical Problem

Accordingly, the present invention has been made keeping in mind the above problem occurring in the related art, and an objective of the present invention is to provide a fixing piece firing device for a dental membrane, the device being capable of firing the fixing piece to fix the dental membrane that covers a graft site after bone graft during implant surgery, and of facilitating access into an oral cavity due to a tip part with a curved front end, thus enabling a quick and easy procedure without using a typical dental drill.

Technical Solution

In order to achieve the above objective, according to one aspect of the present invention, there is provided a fixing piece firing device for a dental membrane, the device including: a linear rod-shaped main body including a tip part and a handle part respectively provided at a front side and a rear side thereof, and a installation space formed inside the main body in a longitudinal direction thereof; a trigger button provided at a junction between the tip part and the handle part so as to be elastically moved outward, and including a through hole centrally formed therein so as to communicate with the installation space such that the through hole and the installation space selectively communicate with each other depending on whether a pressing operation is performed; a hammer provided in the installation space of the handle part so as to be elastically moved forward, and having a front end located in the through hole communicating with the installation space and a rear end protruding outward of the handle part such that when the rear end is pulled, the front end is moved out of the through hole and supported on a rear surface of the trigger button moved elastically outward, causing the hammer to be moved to a loading position, and when the trigger button moved outward is pressed, the through hole is allowed to communicate with the installation space again, causing the hammer to be elastically moved forward to a firing position; and a core provided in the installation space of the tip part, and having a rear end fixedly connected to a front portion of the hammer such that the core is operated in conjunction with loading and firing operations of the hammer, and a front end coming into close contact with a head of a fixing piece located inside the front end of the tip part after the loading operation such that the core pushes the fixing piece toward the dental membrane upon the firing operation.

In the present invention, a front portion of the tip part may be formed in a shape curved in one direction so as to easily access an oral cavity.

In the present invention, a front portion of the core may be made of a flexible coil such that the core is movable inside the tip part having a curved shape.

In the present invention, the trigger button may include a first spring provided at a lower side thereof, and configured such that a first end of the first spring is supported in the installation space while a second end thereof is supported on a lower end of the trigger button, thus allowing the trigger button to be elastically biased outward.

In the present invention, the hammer may be penetrately located in a second spring configured such that a first end of the second spring is supported in the installation space while a second end thereof is supported on the hammer, thus allowing the hammer to be elastically biased forward.

Advantageous Effects

According to the fixing piece firing device for the dental membrane having the above-described configuration, it is possible that the fixing piece is fired to fix the dental membrane, which covers the graft site after bone graft during implant surgery. Furthermore, due to provision of the tip part having the curved front end, it is possible that access to the oral cavity is facilitated, thus enabling a quick and easy procedure without using a typical dental drill.

MODE FOR INVENTION

Hereinbelow, an exemplary embodiment of the present invention will be described in detail with reference to the accompanying drawings such that the present invention can be embodied by one of ordinary skill in the art to which this invention belongs. Various changes to the following embodiment are possible and the scope of the present invention is not limited to the following embodiment.

Figure 1:
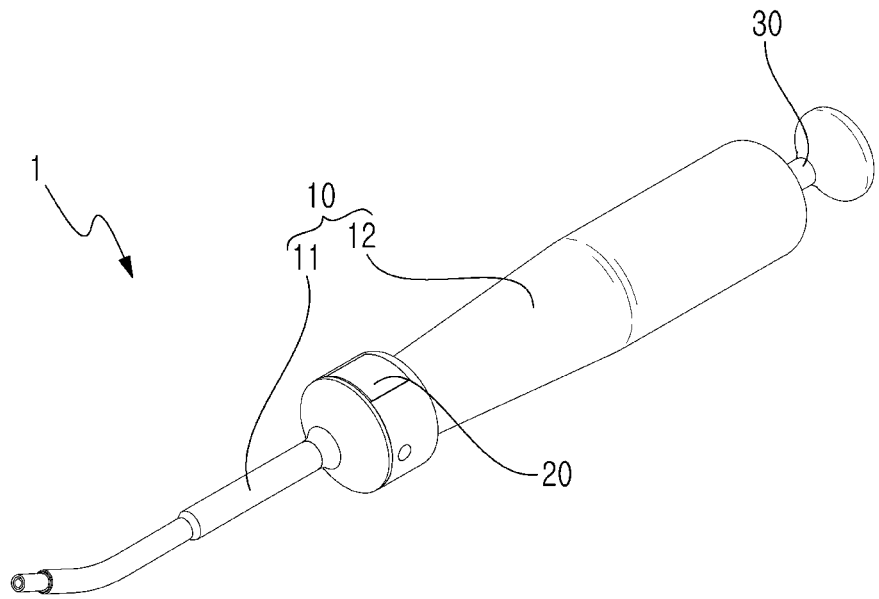
FIG. 1 is a perspective view showing a fixing piece firing device for a dental membrane according to an embodiment of the present invention.
Figure 2:
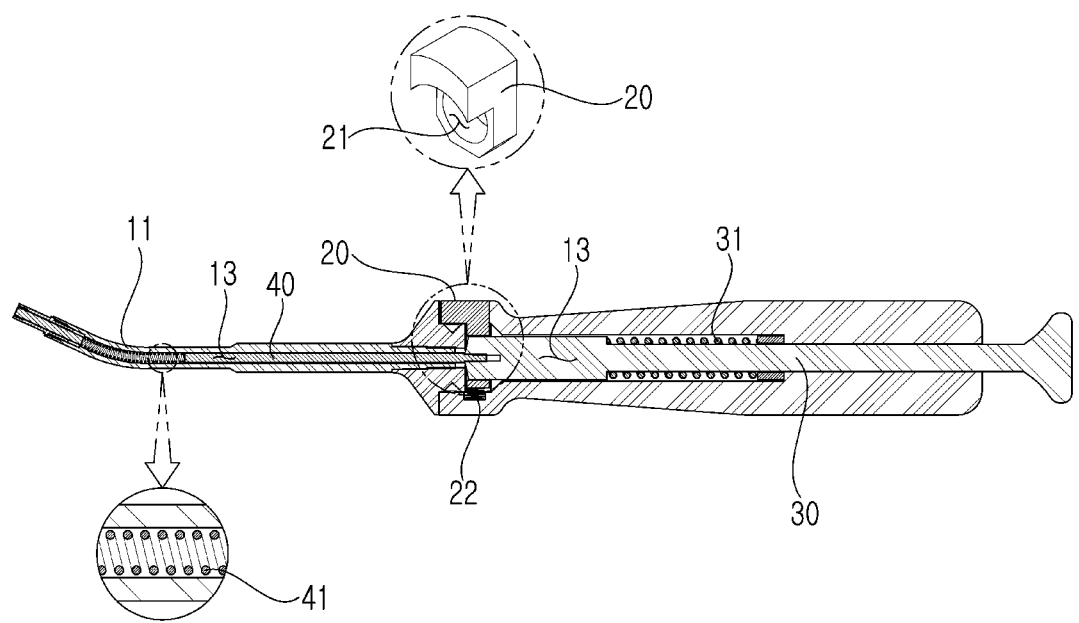
FIG. 2 is a sectional view showing the fixing piece firing device for the dental membrane according to the embodiment of the present invention.
Figure 3:
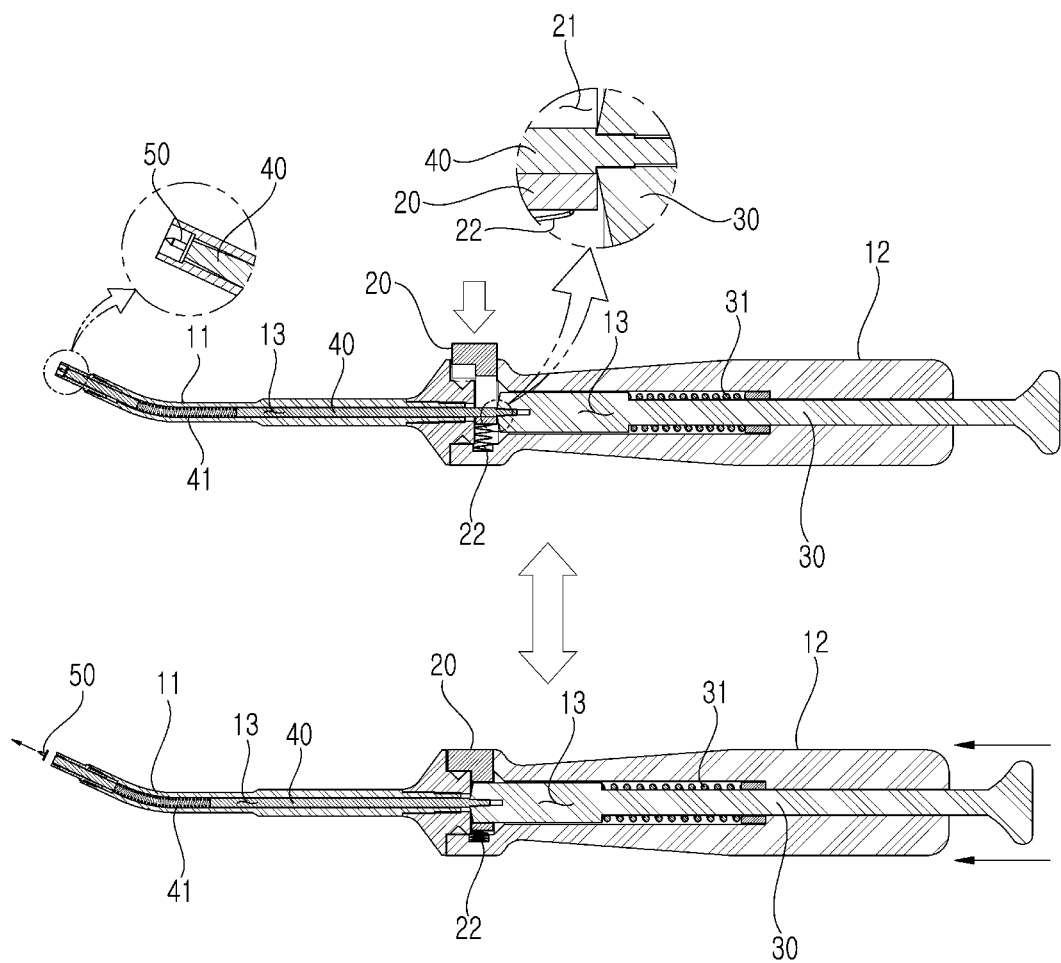
FIG. 3 is a view showing operation of the fixing piece firing device for the dental membrane according to the embodiment of the present invention.
Figure 4:
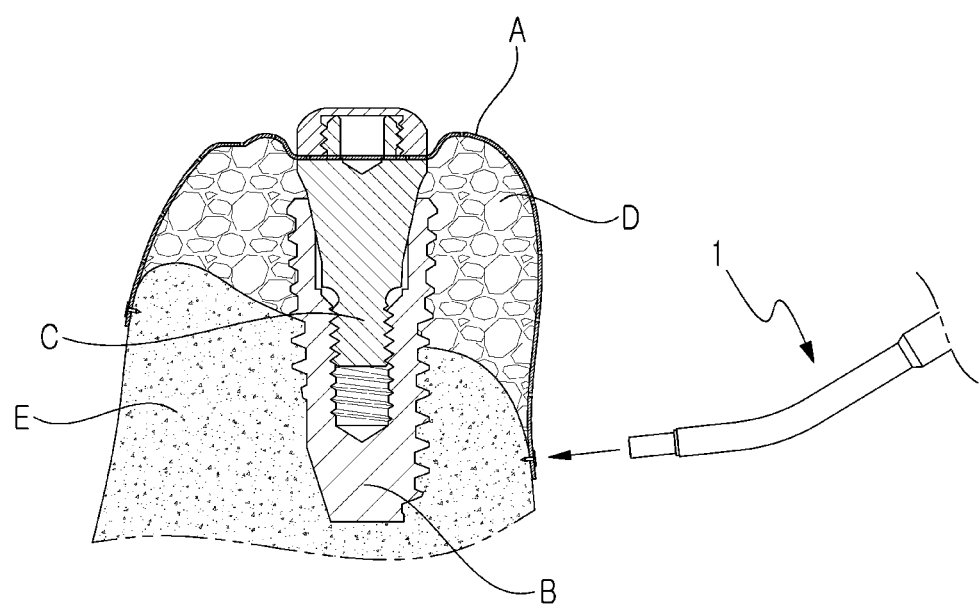
FIG. 4 is view showing a use state of the fixing piece firing device for the dental membrane according to the embodiment of the present invention.

FIG. 1 is a perspective view showing a fixing piece firing device for a dental membrane according to an embodiment of the present invention, FIG. 2 is a sectional view showing the fixing piece firing device for the dental membrane according to the embodiment of the present invention, FIG. 3 is a view showing operation of the fixing piece firing device for the dental membrane according to the embodiment of the present invention, and FIG. 4 is view showing a use state of the fixing piece firing device for the dental membrane according to the embodiment of the present invention.

The fixing piece firing device for the dental membrane according to the embodiment of the present invention includes: a linear rod-shaped main body including a tip part and a handle part respectively provided at a front side and a rear side thereof, and a installation space formed inside the main body in a longitudinal direction thereof; a trigger button provided at a junction between the tip part and the handle part so as to be elastically moved outward, and including a through hole centrally formed therein so as to communicate with the installation space such that the through hole and the installation space selectively communicate with each other depending on whether a pressing operation is performed; a hammer provided in the installation space of the handle part so as to be elastically moved forward, and having a front end located in the through hole communicating with the installation space and a rear end protruding outward of the handle part such that when the rear end is pulled, the front end is moved out of the through hole and supported on a rear surface of the trigger button moved elastically outward, causing the hammer to be moved to a loading position, and when the trigger button moved outward is pressed, the through hole is allowed to communicate with the installation space again, causing the hammer to be elastically moved forward to a firing position; and a core provided in the installation space of the tip part, and having a rear end fixedly connected to a front portion of the hammer such that the core is operated in conjunction with loading and firing operations of the hammer, and a front end coming into close contact with a head of a fixing piece located inside the front end of the tip part after the loading operation such that the core pushes the fixing piece toward the dental membrane upon the firing operation.

Hereinafter, the components of the fixing piece firing device 1 for the dental membrane according to the embodiment of the present invention and a connection relationship between the components will be described in detail with reference to FIG. 1 to FIG. 3.

The main body 10 described above has a profile conforming to the overall shape of the firing device and is operable by a user. The main body 10 is formed in a linear rod shape so as to be easily operable by a user's hand and includes the tip part 11 and the handle part 12 respectively provided at the front and rear sides thereof. Furthermore, the main body includes the installation space 13 formed therein in the longitudinal direction thereof. Although not shown in the drawings, on the outer periphery of the handle part 12, multiple anti-slip protrusions may be formed or a rubber member may be attached, such that a frictional force is provided.

The installation space 13 is configured such that the installation space 13 of the tip part 11 and the installation space 13 of the handle part 12 differ from each other in shape. The installation space of the tip part 11 is in which the core 40 is located and thus is relatively narrow and small to match the size of the core 40, whereas the installation space of the handle part 12 is in which the hammer 30 to be described later is located and thus is relatively wide and large to match the size of the hammer 30.

Furthermore, a front portion of the tip part 11 is formed in a shape curved in one direction. This is to enable a portion of the tip part 11 that is inserted into the oral cavity to easily access any location in the oral cavity. In the present invention, however, the tip part 11 is manufactured in a curved shape in one direction so as not to be orientable. However, the tip part 11 may be manufactured such that the curved direction and curved angle are adjusted by the user.

The trigger button 20 is located at the junction between the tip part 11 and the handle part 12. The trigger button 20 serves as a trigger in such a manner that when the hammer 30 to be described later is moved rearward, the trigger button protrudes outward, causing the hammer 30 to be supported and locked at a rearward position and thus to reach the loading position, and when a protruding portion of the trigger button is pressed, locking of the hammer is released and thus the hammer is elastically moved forward to the firing position.

The trigger button 20 is provided at the junction between the tip part 11 and the handle part 12 so as to be elastically moved outward and includes the through hole 21 centrally formed therein to communicate with the installation space 13. Accordingly, the through hole 21 and the installation space 13 selectively communicate with each other depending on whether the pressing operation is performed, whereby the hammer 30 is supported and locked or is released, between the loading position and the firing position.

The trigger button 20 is provided with a first spring 22 at a lower side thereof to allow the trigger button 20 to be elastically biased outward. That is, a first end of the first spring 22 is supported in the installation space 13 while a second end thereof is supported on a lower end of the trigger button 20 such that when the hammer 30 is moved rearward from the through hole 21, the trigger button 20 is elastically biased outward by the first spring 22, causing the through hole 21 to be moved upward, and a portion of the trigger button 20 where the through hole 21 is not formed supports a front surface of the hammer 30 and thus the hammer 30 is locked in a state of being pulled.

Meanwhile, the hammer 30 is provided in the installation space 13 of the handle part 12 described above. The hammer 30 is moved forward and rearward in the installation space 13, causing a fixing piece 50 to be described later to be loaded and fired. The hammer 30 is provided to be elastically moved forward, and at a ready-to-load position, a front end thereof is located in the through hole 21 communicating with the installation space 13, and a rear end thereof is located at a location protruding outward of the handle part 12. At this time, when the user pulls the rear end of the hammer 30, the front end thereof located in the through hole 21 is moved out of the through hole 21 and supported on the rear surface of the trigger button 20 elastically moved outward, whereby the hammer 30 is moved to the loading position. Furthermore, when the trigger button 20 moved outward is pressed, the through hole 21 is allowed to communicate with the installation space 13 again, whereby the hammer is elastically moved forward to the firing position. It is preferable that the rear end of the hammer 30 has an extension so as to be easily pulled by a user.

Furthermore, the hammer 30 described above is penetrate located in a second spring 31 provided in the installation space 13. The second spring 31 elastically biases the hammer 30 forward. To this end, a first end of the second spring 31 is supported in the installation space 13 while a second end thereof is supported on the hammer 30. Accordingly, when the hammer 30 is moved rearward, the second spring 31 is compressed, and when the hammer 30 is moved forward, energy of the compressed second spring 31 is converted into energy for pushing the hammer 30, causing the hammer to be biased forward.

The core 40 is provided in the installation space 13 of the tip part 11 described above. The core 40 is moved forward and rearward in the installation space 13 in conjunction with the hammer 30 and thus directly pushes the head of the fixing piece 50 to be described later, causing the fixing piece 50 to be fired.

The core 40 is located in the installation space 13 of the tip part 11 while a rear end thereof is fixedly connected to the front portion of the hammer 30 and thus the core is operated in conjunction with the loading and firing operations of the hammer 30. Furthermore, the front end of the core comes into close contact with the head of the fixing piece 50 located inside the front end of the tip part 11 after the loading operation, whereby the core pushes the fixing piece 50 toward the dental membrane upon the firing operation. At this time, a front portion of the core 40 is made of a flexible coil 41 such that the core is movable inside the tip part 11 having a curved shape.

Hereinafter, referring to FIG. 4, a method of using the fixing piece firing device 1 for the dental membrane according to the embodiment of the present invention will be described in detail.

First, when the user pulls the hammer 30 and the hammer 30 is moved rearward, the trigger button 20 is elastically biased outward by the first spring 22, causing the through hole 21 to be moved upward while causing a lower portion of the trigger button 20 where the through hole 21 is not formed to support the front surface of the hammer 30, whereby the hammer 30 is locked in a state of being pulled, thus reaching the loading position.

Then, the fixing piece 50 for fixing the dental membrane A is loaded into the front end of the tip part 11. Meanwhile, a bone graft material D is added to partial outer surfaces of a fixture B and an abutment C inserted in an alveolar bone E, and the bone graft material D is covered by the dental membrane A placed thereover. At this time, a lower portion of the dental membrane A is located on the alveolar bone E.

Then, when the trigger button 20 moved outward of the main body 10 is pressed with the tip part 11 being placed close to the dental membrane A in the oral cavity, the through hole 21 is allowed to communicate with the installation space 13 again, whereby the hammer 30 is elastically moved forward. At this time, the core 40 connected to the hammer 30 is also moved forward, causing the head of the fixing piece 50 in close contact with the front end of the core 40 to be pushed, thus firing the fixing piece 50, whereby the dental membrane A is firmly fixed to the alveolar bone E by the fired fixing piece 50.

According to the fixing piece firing device 1 for the dental membrane as described above, it is possible that the fixing piece 50 is fired to fix the dental membrane A, which covers a graft site after bone graft during implant surgery. Furthermore, due to provision of the tip part 11 having the curved front end, it is possible that access to the oral cavity is facilitated, thus enabling a quick and easy procedure without using a typical dental drill.

While the exemplary embodiment of the invention has been described above, the embodiment is only an example of the invention, and it will be understood by those skilled in the art that the invention can be modified in various forms without departing from the technical spirit of the invention. Therefore, the scope of the invention should be determined on the basis of the descriptions in the appended claims, not any specific embodiment, and all equivalents thereof should belong to the scope of the invention.

DESCRIPTION OF THE REFERENCE NUMERALS IN THE DRAWINGS

1: fixing piece firing device for dental membrane
10: main body
11: tip part
12: handle part
13: installation space
20: trigger button
21: through hole
22: first spring
30: hammer
31: second spring 40: core
41: coil
50: fixing piece
A: dental membrane
B: fixture
C: abutment
D: bone graft material
E: alveolar bone

The invention claimed is:

1. A fixing piece firing device for a dental membrane, the device comprising:
  a linear rod-shaped main body (10) including a tip part (11) and a handle part (12) respectively provided at a front side and a rear side thereof, and a installation space (13) formed inside the main body in a longitudinal direction thereof;
  a trigger button (20) provided at a junction between the tip part (11) and the handle part (12) so as to be elastically moved outward, and including a through hole (21) centrally formed therein so as to communicate with the installation space (13) such that the through hole (21) and the installation space (13) selectively communicate with each other depending on whether a pressing operation is performed;
  a hammer (30) provided in the installation space (13) of the handle part (12) so as to be elastically moved forward, and having a front end located in the through hole (21) communicating with the installation space (13) and a rear end protruding outward of the handle part (12) such that when the rear end is pulled, the front end is moved out of the through hole (21) and supported on a rear surface of the trigger button (20) moved elastically outward, causing the hammer to be moved to a loading position, and when the trigger button (20) moved outward is pressed, the through hole is allowed to communicate with the installation space (13) again, causing the hammer to be elastically moved forward to a firing position; and
  a core (40) provided in the installation space (13) of the tip part (11), and having a rear end fixedly connected to a front portion of the hammer (30) such that the core is operated in conjunction with loading and firing operations of the hammer (30), and a front end coming into close contact with a head of a fixing piece (50) located inside the front end of the tip part (11) after the loading operation such that the core pushes the fixing piece (50) toward the dental membrane upon the firing operation,
  wherein a front portion of the tip part (11) is formed in a shape curved in one direction so as to easily access an oral cavity and
  wherein a front portion of the core (40) is made of a flexible coil (41) such that the core is movable inside the tip part (11) having a curved shape.

2. The device of claim 1, wherein the trigger button (20) includes:
  a first spring (22) provided at a lower side thereof, and configured such that a first end of the first spring is supported in the installation space (13) while a second end thereof is supported on a lower end of the trigger button (20), thus allowing the trigger button (20) to be elastically biased outward.

3. The device of claim 1, wherein the hammer (30) is penetrately located in a second spring (31) configured such that a first end of the second spring is supported in the installation space (13) while a second end thereof is supported on the hammer (30), thus allowing the hammer (30) to be elastically biased forward.

* * * * *